US00PP18568P3

(12) United States Plant Patent
Recupero et al.

(10) Patent No.: US PP18,568 P3
(45) Date of Patent: Mar. 11, 2008

(54) MANDARIN TREE NAMED 'TOP MANDARIN SEEDLESS'

(50) Latin Name: *Citrus reticulata*
Varietal Denomination: Top mandarin seedless

(75) Inventors: Giuseppe Reforgiato Recupero, Acireale (IT); Giuseppe Russo, Acireale (IT); Santo Recupero, Acireale (IT)

(73) Assignee: Future Fruit, LLC, Visalia, CA (US)

( * ) Notice: Subject to any disclaimer, the term of this patent is extended or adjusted under 35 U.S.C. 154(b) by 0 days.

(21) Appl. No.: 11/322,815

(22) Filed: Dec. 30, 2005

(65) Prior Publication Data

US 2006/0179524 P1 Aug. 10, 2006

Related U.S. Application Data

(60) Provisional application No. 60/646,008, filed on Jan. 21, 2005.

(51) Int. Cl.
*A01H 5/00* (2006.01)

(52) U.S. Cl. ..... Plt./201

(58) Field of Classification Search ..... Plt./201
See application file for complete search history.

*Primary Examiner*—Kent Bell
*Assistant Examiner*—Annette Para
(74) *Attorney, Agent, or Firm*—Mark D. Miller

(57) ABSTRACT

A new and distinct seedless mandarin named 'Top Mandarin Seedless' characterized by late bearing in January through to February in the citrus areas of Sicily, Italy and Riverside, Calif. The tree has high yields and bears from years three onwards. It is further characterized by being a triploid and genetically seedless. The fruit is well sized having a typical mandarin shape (round, flattened) and has acceptable rind thickness with a smooth texture. The fruit stores well, and has reddish pigmented flesh, good acid-sugar ratios, and good external color. The fruit has an average juice content of about 40–50% at harvest.

12 Drawing Sheets

*(Citrus reticulata).*

BACKGROUND OF THE NEW VARIETY

The present invention refers to a new late harvesting variety of triploid pigmented mandarin which will hereinafter be denominated as the 'Top Mandarin Seedless.' The 'Top Mandarin Seedless' tree produces commercially seedless mandarin fruit, bearing in late January through to February in the citrus areas of Sicily, Italy. The 'Top Mandarin Seedless' trees are triploids, having three sets of chromosomes. The trees bear from year three and have consistent year-to-year bearing habits, the fruit has acceptable rind thickness, acid-sugar ratios and color, and has an average juice content of 40–50% at harvest.

In the development of new commercial fruit varieties, specific characteristics provide a premium on those fruit varieties that mature late or late in the growing season. For a new fruit variety to be a commercial success, the fruit must be of good size, good color, and also have good holding/storage as well as advantageous harvest times and shipping characteristics. In addition, the date of maturing is preferably different from other similar fruit. This new invention meets all of the aforementioned criteria and therefore would be of commercial appeal to the consumer.

The Top Mandarin seedless variety is a triploid sexual hybrid. Polyploidy in citrus is well known (pp. 191–193, Speigel-Roy & Goldschmidt, 1996). *Citrus* and related genera are typically diploidic and have two sets of 9 chromosomes (2n=18). Triploids, tetrapoid and hexaploids exist naturally but occur in low percentages in the population. *Citrus* triploids are cytologically recognizable by the presence of an additional set of chromosomes. In some cases, triploids are also morphologically recognizable.

ORIGIN AND ASEXUAL REPRODUCTION OF THE NEW VARIETY

The invention (variety) comprises a new and distinct variety of a seedless mandarin plant named 'Top Mandarin Seedless' discovered by the inventors in Azienda Palazzelli Lentini (SR), Sicily, Italy in 1998. The new invention is a triploid (3n=27 chromosomes) selection from sexual crosses made between a tetraploid (pollen) male parent ('Tarocco Orange' unpatented) and a diploid (seed bearing) female parent ('Clementine mandarin' var. 'Clemenules' unpatented) and named 'Top Mandarin Seedless.' The new invention was subsequently asexually reproduced by the inventors in 2000 by bud grafting on to 'Sour Orange' root stock. The resulting trees were experimentally evaluated, and the resulting tree growth was strong with no bud union abnormalities being noted on the 'Sour Orange' rootstock. An additional 10 trees were asexually reproduced by the inventors in 2003 by bud grafting on to 'Sour Orange' root stock and grown in Riverside, Calif. The inventors carefully compared all of the asexually reproduced trees with the parent tree including the fruit and found, thus far, that they are identical in all respects. The trees under evaluation are free from all known viruses and viroids including; Tristeza, Exocortis, Xyloporosis and Psorosis.

SUMMARY OF THE NEW VARIETY

The 'Top Mandarin Seedless' is particularly characterized by being a triploid, genetically (and hence commerically) seedless, good fruit size, precocious with stable year to year high yields and a late bearing variety (January/February) in Northern Hemisphere citrus bearing regions. The internal fruit quality is excellent and has a pigmented flesh.

DETAILED DESCRIPTION

Referring more specifically to the horticultural details of the new and distinct variety of mandarin, the following descriptions have been observed under the ecological conditions prevailing at the origin orchard which is located in Sicily, Italy as well as in Riverside, Calif. Color references are to the Dictionary of Color by Maerz and Paul, First Edition published in 1930. Common colors are also employed.

TREE

Size: Medium, for $4^{th}$ year tree.
- *Height.*—8–10 feet.
- *Width.*—6–8 feet at drip line.

Shape: Upright, growth habit when grown on 'Sour Orange' rootstock.

Growth: Dense; vigorous branches tend to grow out, upward beyond trees' general periphery; abundant axillary and accessory bud development.

Vigor: Medium.

Productivity: Acceptable for $4^{th}$ year tree with slight alternate bearing tendencies; fruit produced on the outside and inside of the canopy.

TRUNK

Immediately above the rootstock interface on 'Sour Orange':
- *Size.*—Circumference of 10–14 inches, 18 inches above ground.
- *Surface texture.*—Smooth.
- *Color.*—4 year old tree, Andover green (23-E-2).
- *Lenticels.*—100–200 per sq. cm.

BRANCHES

Size: Scaffold (structural) branches, circumference of 8–10 inches; Secondary branches (on which fruit bearing branches are borne) circumference of 3–5 inches.

Angle of branches: Average between about 30° and about 40°.

Color of branches over 2 years old: Andover green (23-E-2).

Color of branches less than 2 years old: Brunswick green, $LT^P$ (22-L-10).

Figure 5:
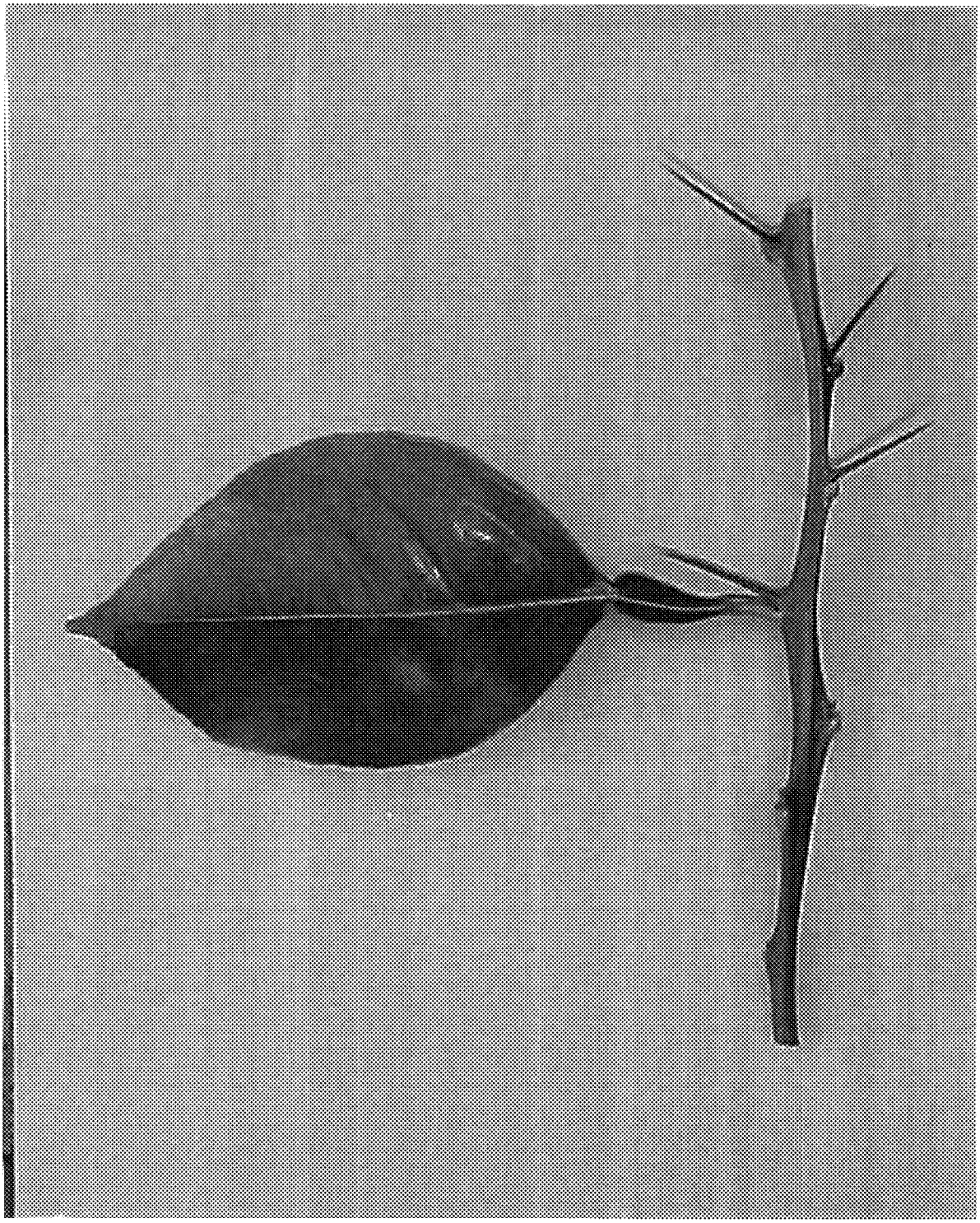
FIG. 5 is a color photograph showing a typical view of the leaf arrangement on a one year old thorny branch of the present invention.

Thorns: Many on young branches (See FIG. 5.).
- *Length.*—20–30 mm (0.8–1.2 in.).
- *Width.*—2–3 mm (0.08–0.12 in.) at base.

LEAVES

Figure 4:
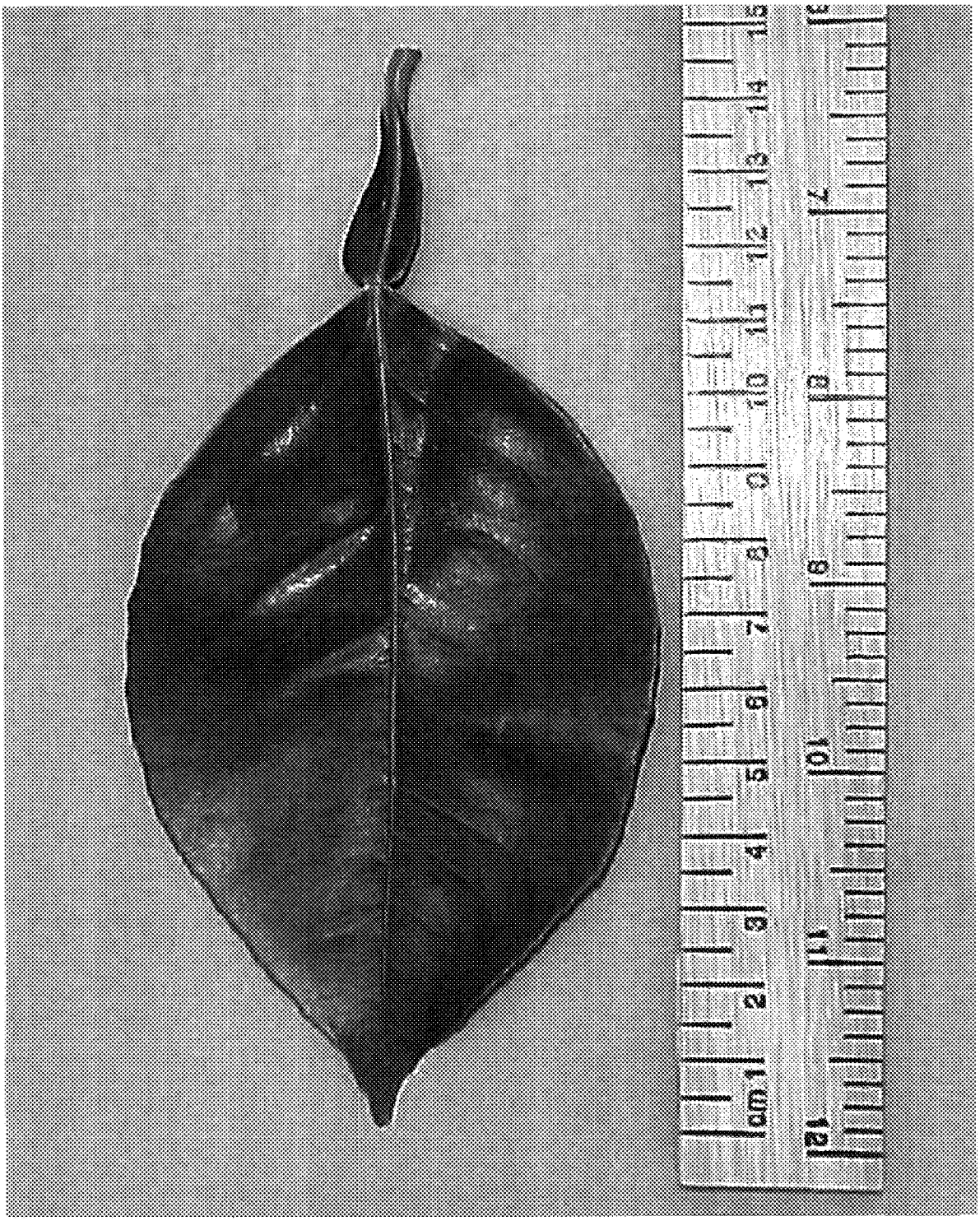
FIG. 4 is a color photograph showing a typical view of a leaf of the present invention (with ruler for scale).
Figure 6:
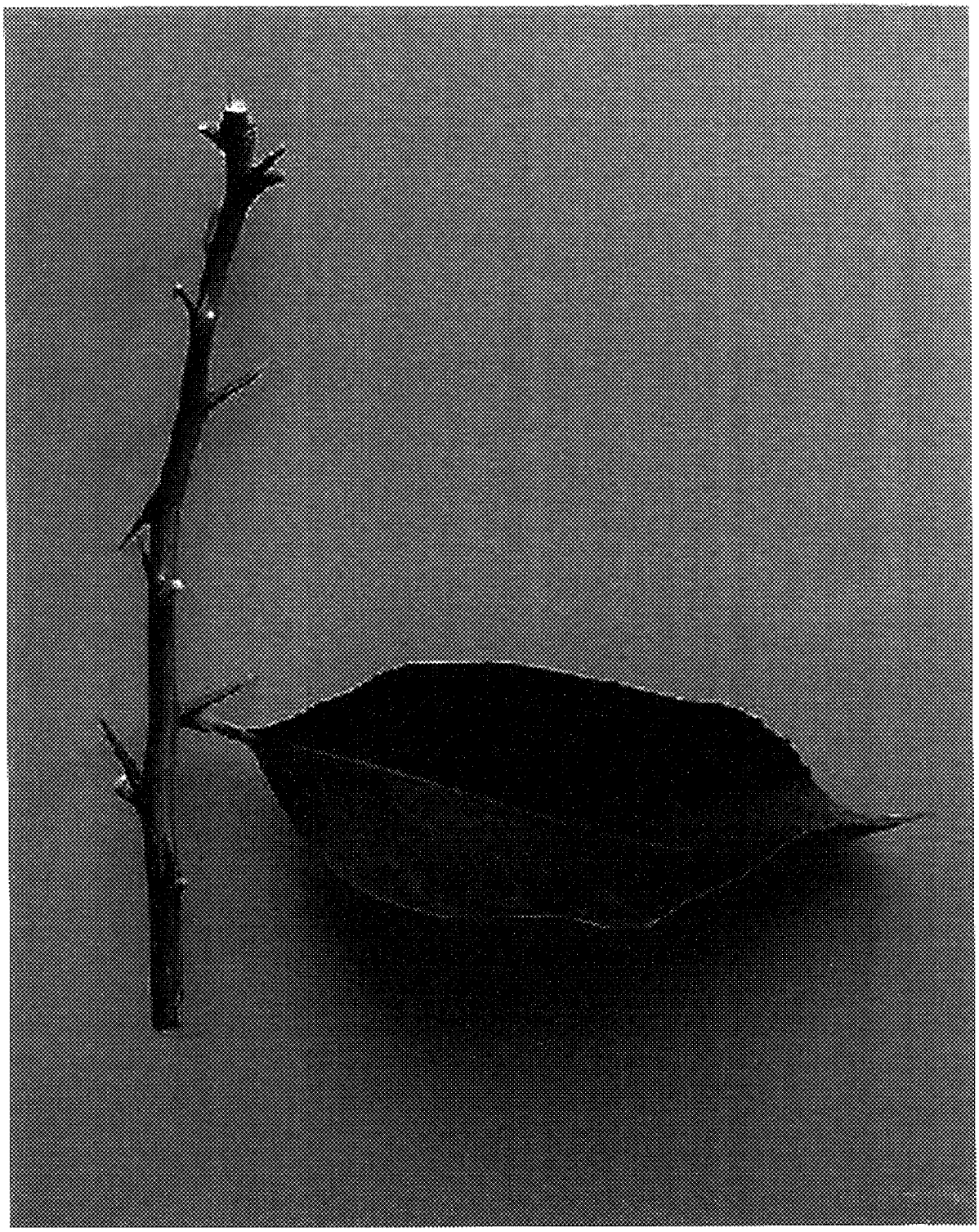
FIG. 6 is a color photograph showing a typical view of a two year (juvenile) branch showing reduced thorns.
Figure 7:
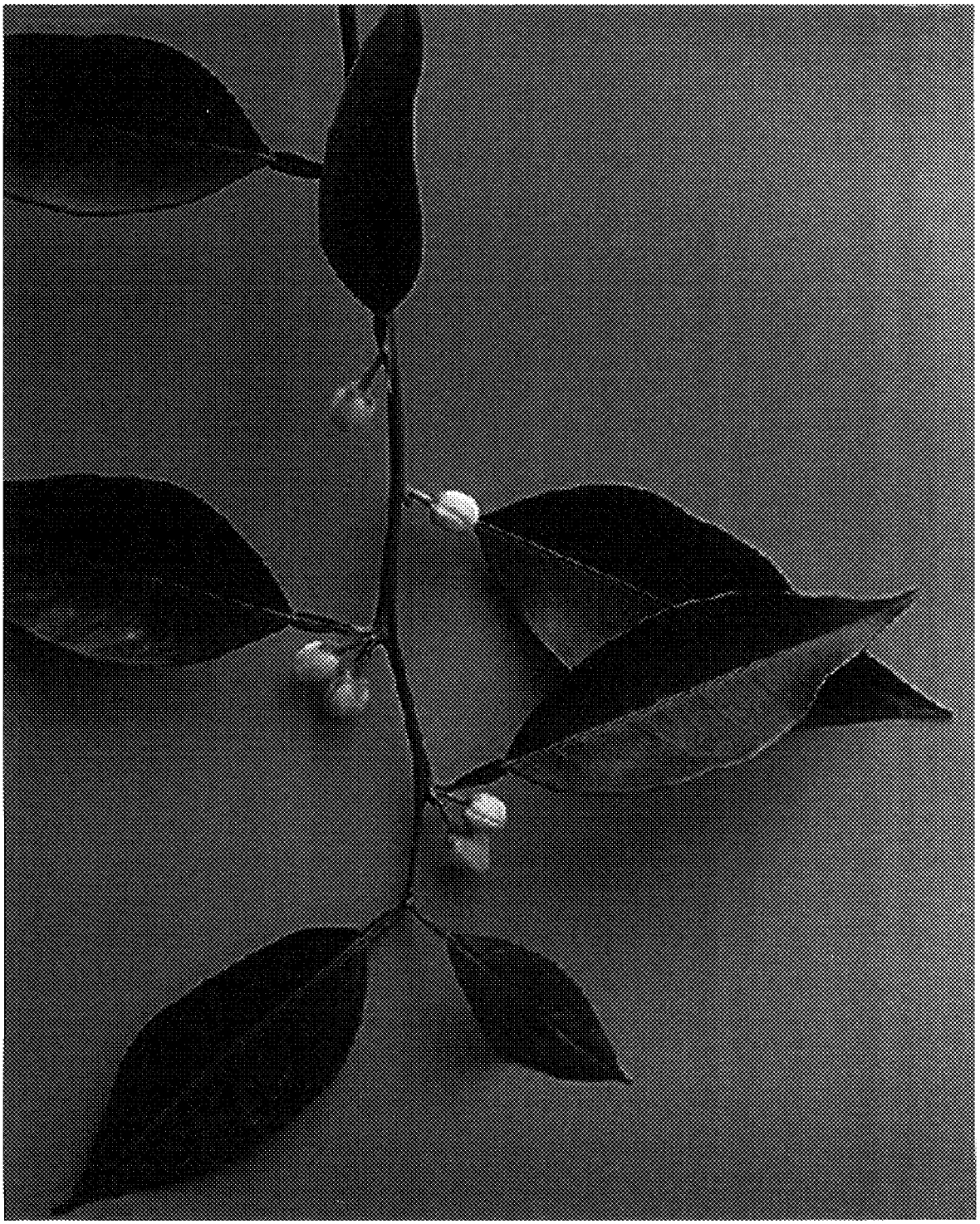
FIG. 7 is a color photograph showing a typical view of leaf and flower arrangement on a fruiting branch. Note the absence of thorns.
Figure 8:
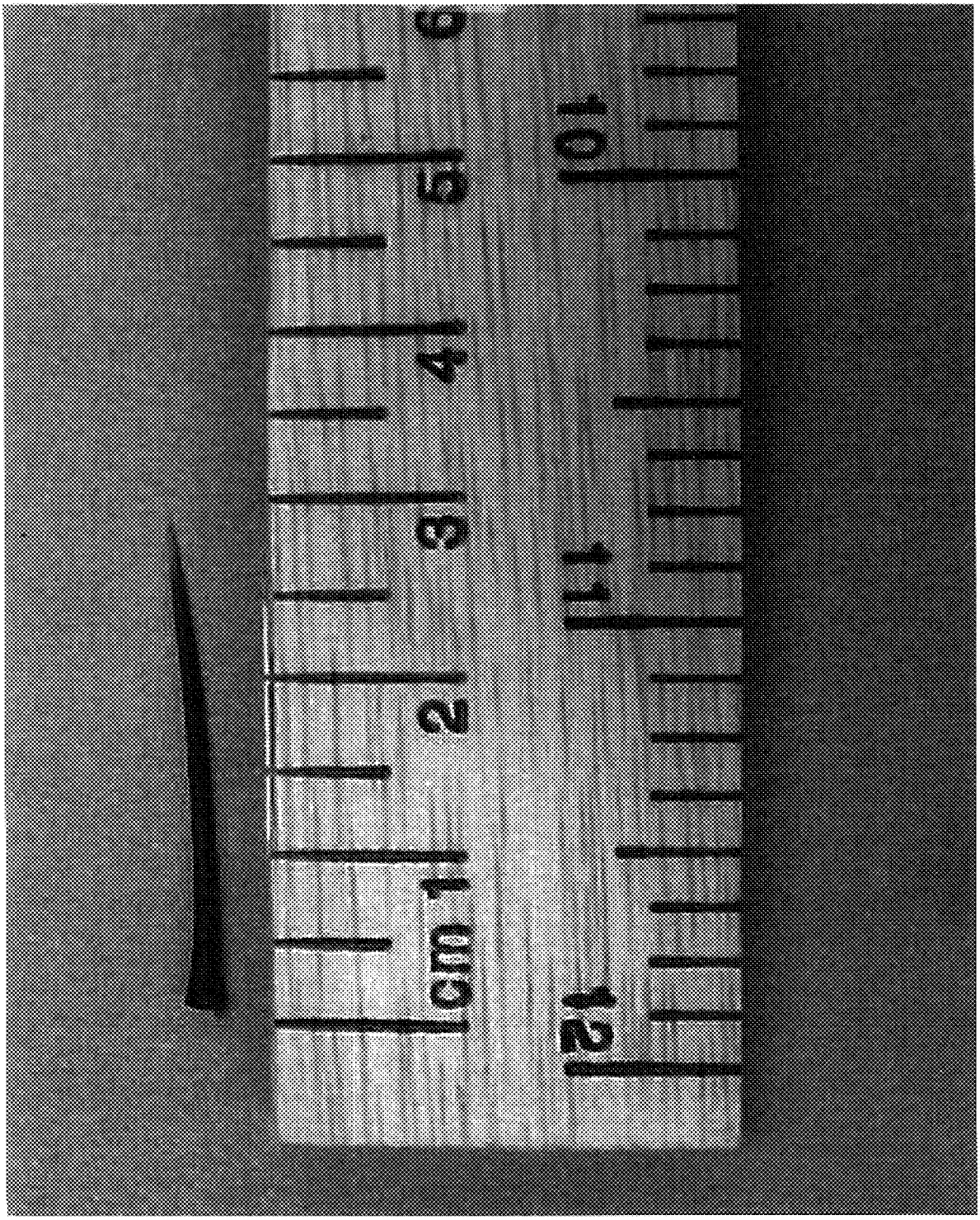
FIG. 8 is a color photograph showing a typical thorn produced on a one year old branch (with ruler for scale).
Figure 9:
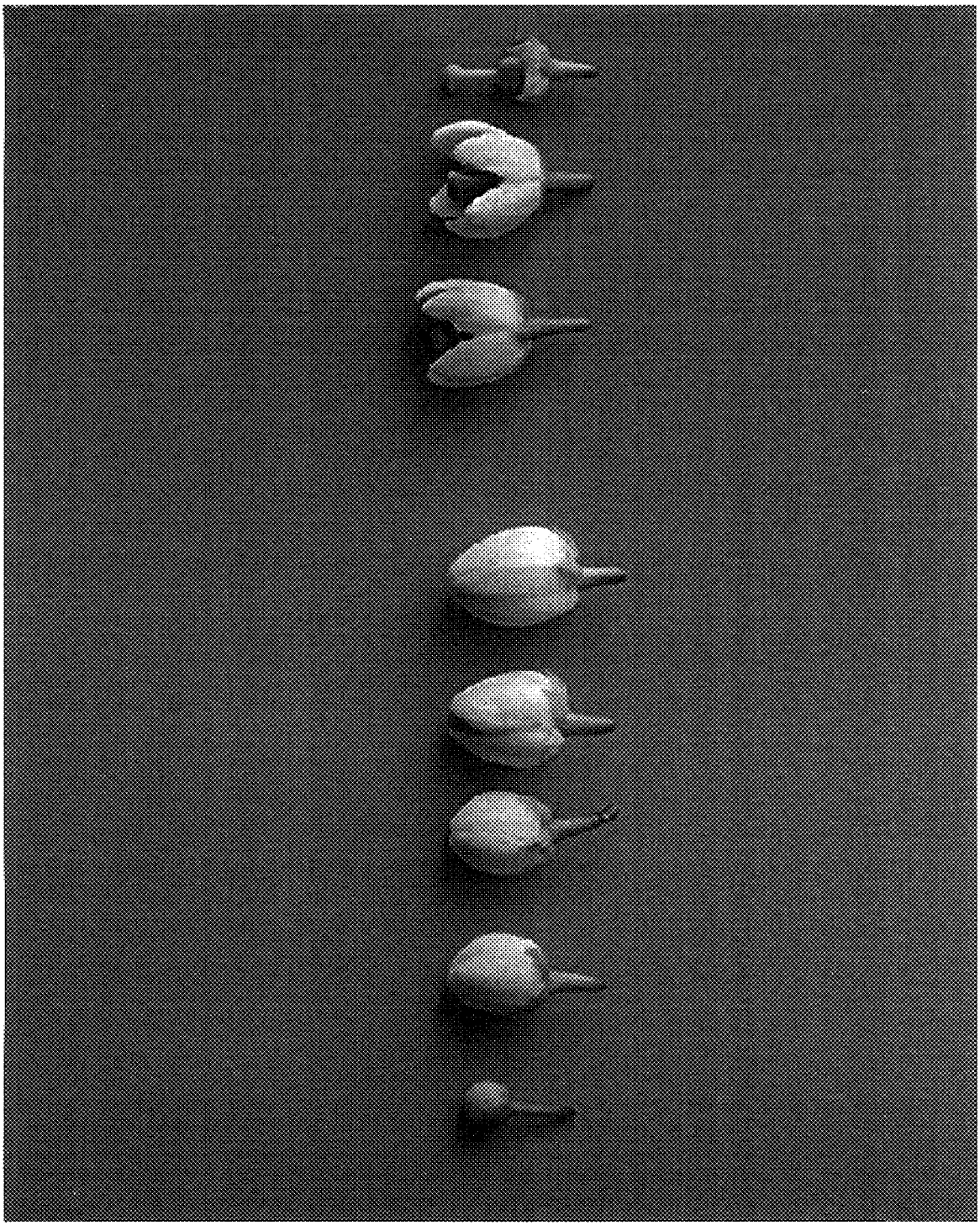
FIG. 9 is a color photograph showing a typical white flowers with the complete absence of authocyanin development. On the far left is an unopened flower and on the far right is a fruitlet.
Figure 10:
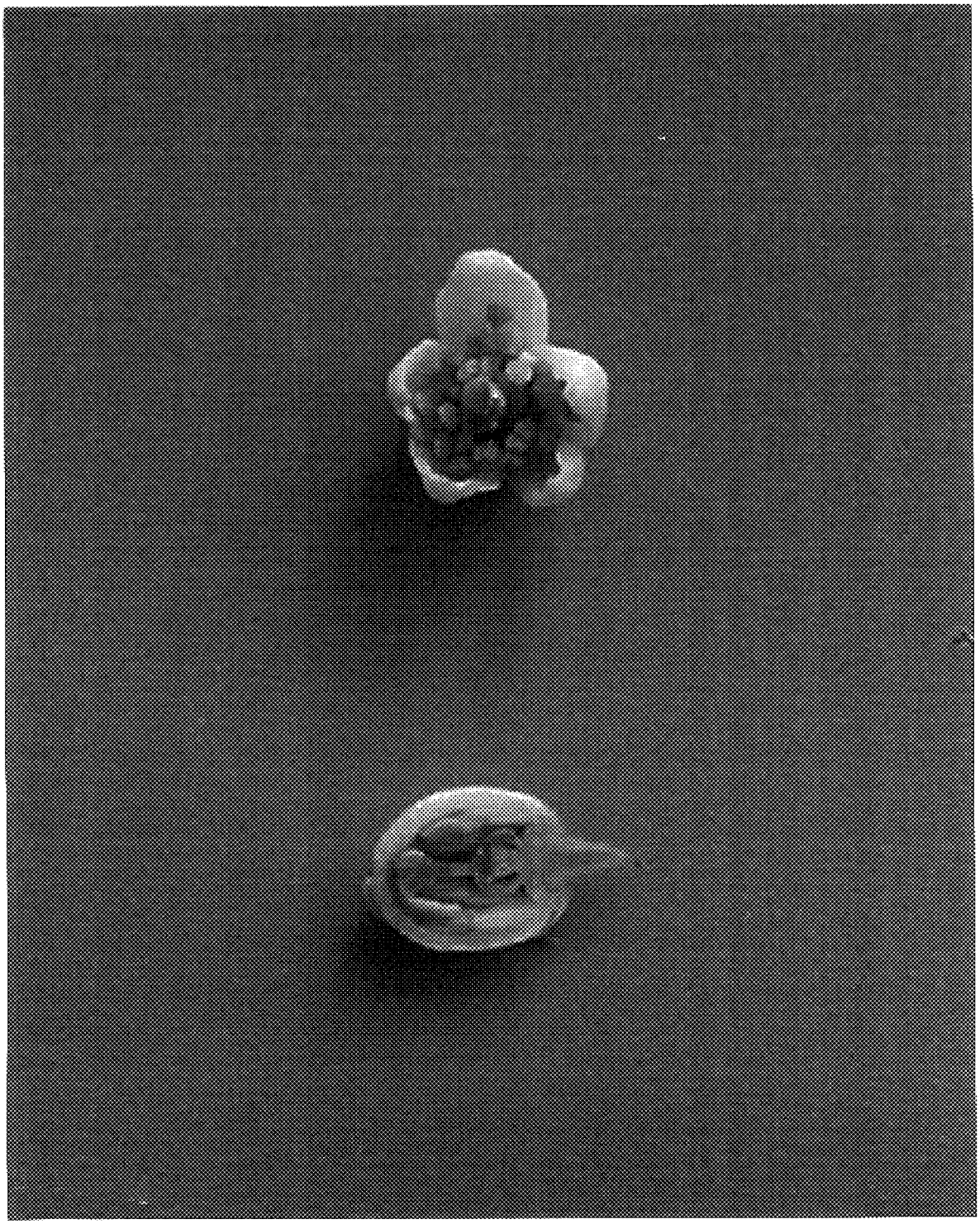
FIG. 10 is a color photograph showing a top and longitudinal section of a typical flower.
Figure 11:
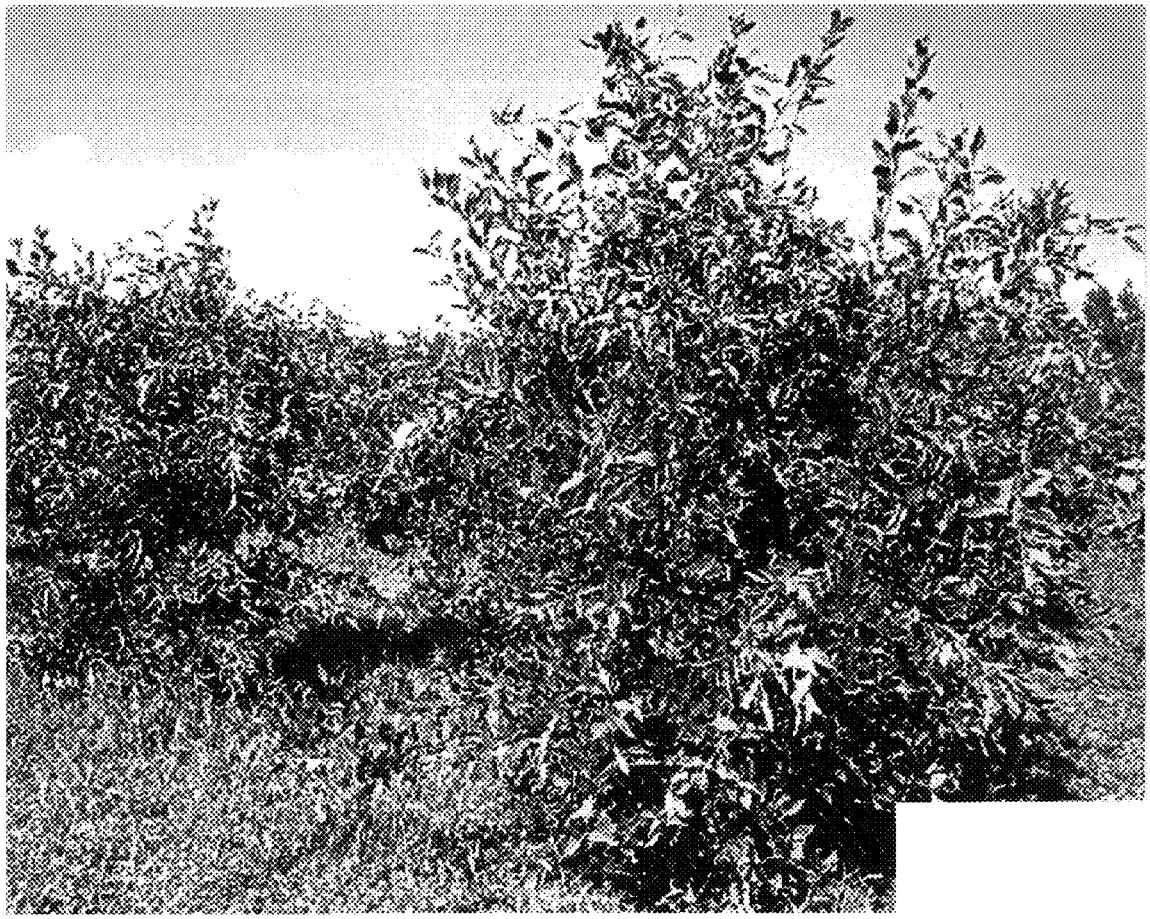
FIG. 11 is a color photograph showing an overall view of a three year old tree.
Figure 12:
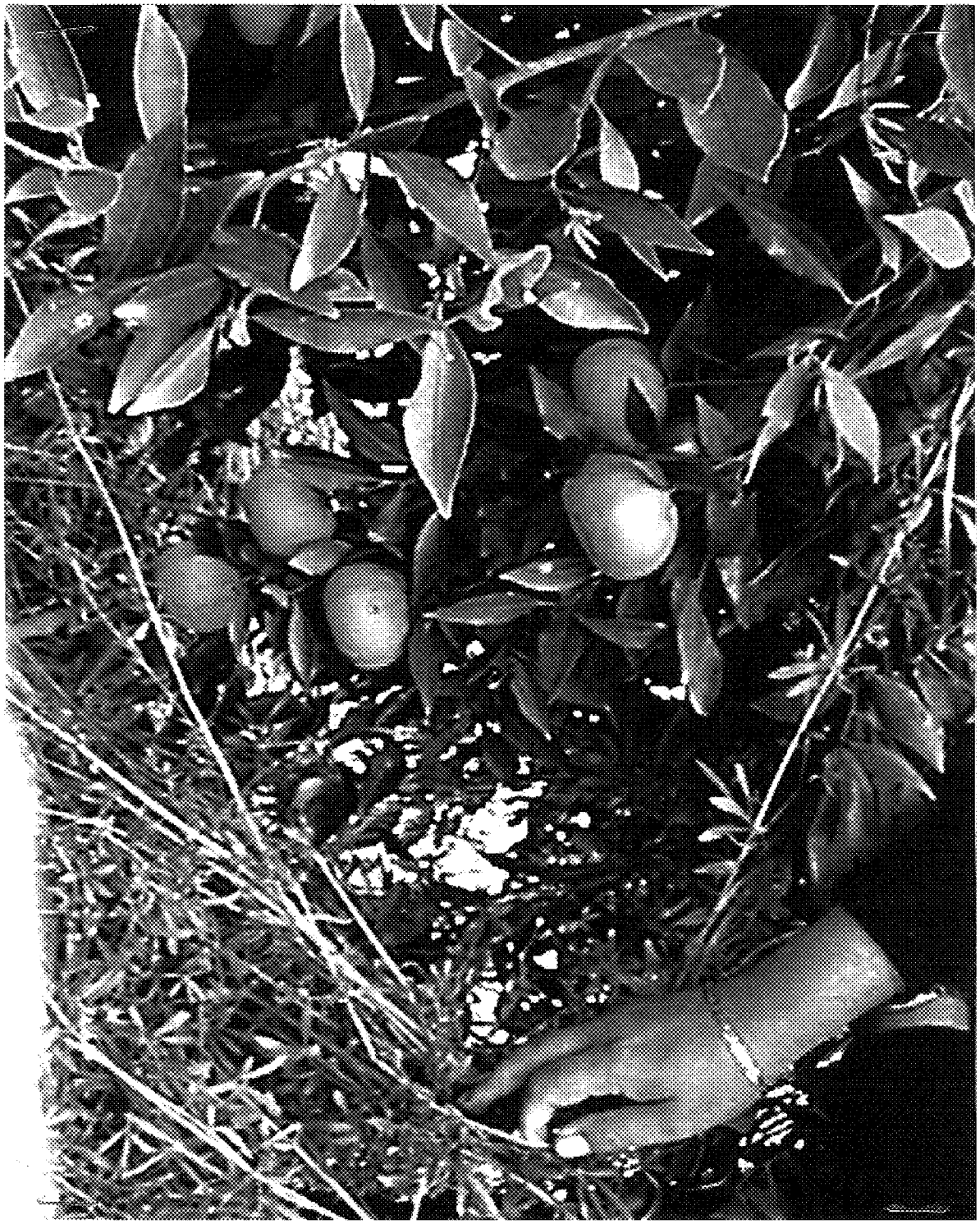
FIG. 12 is a color photograph showing typical fruit production on three year old tree with a high incidence of terminal fruit.

The leaves are alternate, unifoliate with distinct articulation between the petiole and leaf blade. They exhibit a slight curvate morphology along the longitudinal axis without significant undulation, and have prominent basal wings when juvenile (See FIGS. 4–5). The wings become much less prominent as the tree matures (FIGS. 6–7).

Size: Medium.
- *Length.*—120–160 mm (4.8–6.4 in.).
- *Width.*—60–80 mm (2.4–3.2 in.).

Texture: Smooth, lacking depressions in the adaxial surface. Abaxial surface has raised leaf veins.

Shape: Elliptically oval to oblong. Acute tips (See FIG. 4).

Margin: Mild serrations at edge.

Apex: Minor crenation on acute leaf tip.

Base: Slightly elongated.

Edges: Distinctly smoother towards the basal leaf end.

Marginal oil cells: Many 8–10 per linear cm; oil cells are ovoid and smooth.

Color: Mature leaves glossy.
- *Upper surface.*—Alfalfa Green (22-C-12).
- *Lower surface.*—Piquant Green (20-K-6).
- *Petioles.*—Has prominent wings (See FIG. 4).
- *Length.*—25–40 mm (1–1.6 in).
- *Diameter.*—Approximately 10 mm (0.4 in.).
- *Color.*—Alfalfa Green (22-C-12).

Venation: Distinct, pinnately reticulated.

Midvein:
- *Width.*—At base, 1–2 mm (0.04–0.08 in.); Width at apex 0.3 mm–0.4 mm (0.012–0.016 in.).
- *Color.*—Chrome Green $LT^P$ (22-L-12).

FLOWERS

The flowers are small and complete. Flower buds have little or no anthocyanin coloration during development. Flowers are borne in single or multiple clusters. Anther color is pale yellow to yellow. Pollen fertility is very low to sterile as indicated by the observation that less than <0.01% of the pollen grains stained with acetocarmine. The flowers have a sweet pleasing citrus fragrance.

Flower buds:

*Shape.*—10 days prior to anthesis, slightly ovoid, 10 mm (0.4 in.) diameter 1–2 days prior to flowering, elongated cone, 10–12 mm (0.4 in.) diameter, Average length — 15–20 mm (0.6–0.8 in.).

Calyx: 4–5 sepals, fused forming a cup-like calyx.

*Color.*—Calliste green (19-L-6). Lobe tips are blunt but with apiculate tips.

Date of normal first bloom:

*Sicily, Italy.*—First bloom: about March 15$^{th}$; end bloom about April 15$^{th}$ Riverside, Calif.: First bloom about April 1$^{st}$, end bloom about April 20$^{th}$.

Flowers: Medium — in clusters of three to five.

*Diameter when fully opened.*—20–30 mm (0.81–1.2 in.).

*Bloom.*—E.g. quantity — abundant (typical of a mandarin) non-alternate bearing.

Petals: 4–5, rounded tips.

*Size.*—Small (compared to other citrus species). Length: 12–16 mm (0.48–0.64 in.). Width: 4–7 mm (0.16–0.28 in.).

*Form.*—Narrow, linear, slightly oblong.

*Color.*—Adaxial surface — white (1-A-1). Abaxial surface — white (1-A-1).

*Claws.*—None.

*Petal margins.*—Smooth, rounded at tips.

*Pedicel.*—4–6 mm (0.16–0.24 in.) average. Color: Sea green (19-K-6).

*Sepals.*—Color: Glass green (18-F-3).

*Stamen.*—Number: 15–20, with complete style development. Length 10–15 mm. Filament: white (10-A-1). Anthers: 2–4 mm (0.08–0.16 in.) length; 1–2 mm (0.04–0.08 in.) width. Color: Aureolin$^{P}$ (10-L-2).

*Pistil.*—Stigma: ovoid shape, 2.5–3 mm (0.1–0.12 in.) diameter; Color: Pineapple (11-J-2). Style: 6–10 mm (0.24–0.4 in.) length; 2–3 mm (0.08–0.12 in.) wide; Color: Sea foam Y (17-C-2). Ovary: 6–8 mm (0.24–0.32 in.) diameter; ovoid shape; Color: Imperial jade (21-L-12).

FRUIT

On grafted trees the first fruit production occurred after three seasons. Internal characteristics: The fruit flesh is has a gradient of red pigmentation being most intense near the albedo and diminishing towards the fruit core. (See FIGS. 1–2.) The fruit is seedless. There is no persistence of the style on the fruit.

Internal characteristics:

*Flesh color.*—Near rind, Redfeather Buddha (4-L-11). Remainder, Bitter Sweet O — (3-B-12).

*Interior segments.*—Average of 9 to 12 in number. Interior segment membranes — thin.

*Pulp vesicles.*—Medium, 6–8 mm (0.24–0.32 in.) length; 2 mm (0.08 in.) diameter; color: Bitter Sweet O — (3-B-12).

*The septa.*—Dorsal slightly convex contoured character. Slight separation in the middle Juice — abundant in mature fruit (40–50% at harvest), evenly distributed in sections, typical mandarin flavor: rich, with low acid and high sugar (10–13 BRIX at harvest, Sugar acid ratio at harvest>8), well blended (pH is 3.3–3.8). The fruit center exhibits separation, with a diameter of approximately 6–10 mm. Rind oil cells are medium to large, and occur at a density of approximately 150–200 per cm$^2$. Glandular layer 2–3 mm (0.08–0.12 in.). Mesocarp (albedo) — 5–8 mm (0.2–0.32 in.).

*Axis.*—5–6 mm (0.2–0.24 in.) diameter.

*Fruit weight.*—Average of 140 g–160 g (mean of 100 fruit per tree and 5 trees).

*Date of maturity.*—Sicily, Italy about January 15$^{th}$–January 30$^{th}$. Riverside Calif.: about February 1$^{st}$–Feburary 15$^{th}$.

External characteristics:

*Size.*—Medium. Length: 50–60 mm (2–2.4 in.). Width: 60–70 mm (2.4–2.8 in.).

Figure 1:
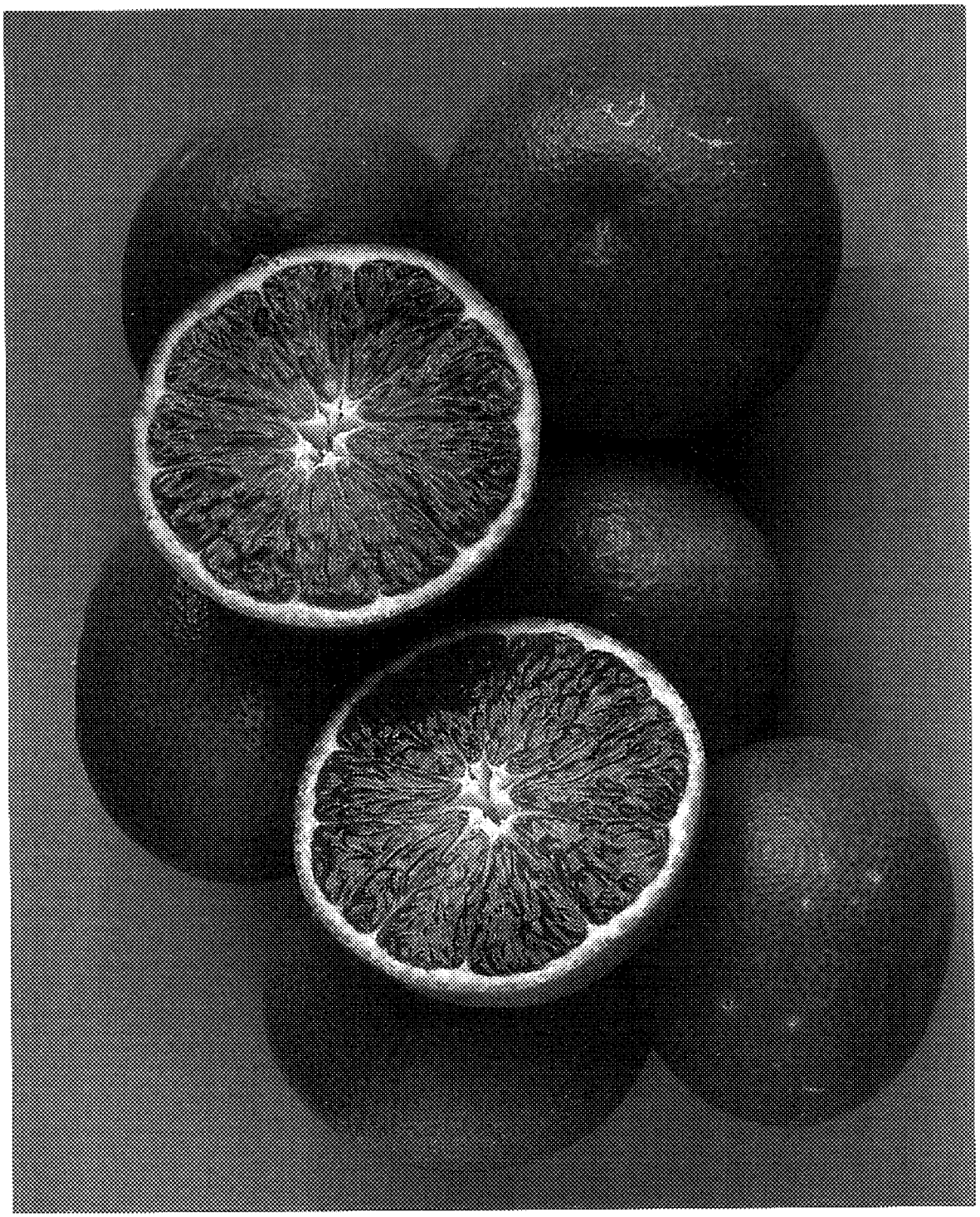
FIG. 1 is a color photograph showing an overall perspective view of several specimens of typical whole fruit, and one transversely cut fruit of the present invention harvested in January 2004.
Figure 2:
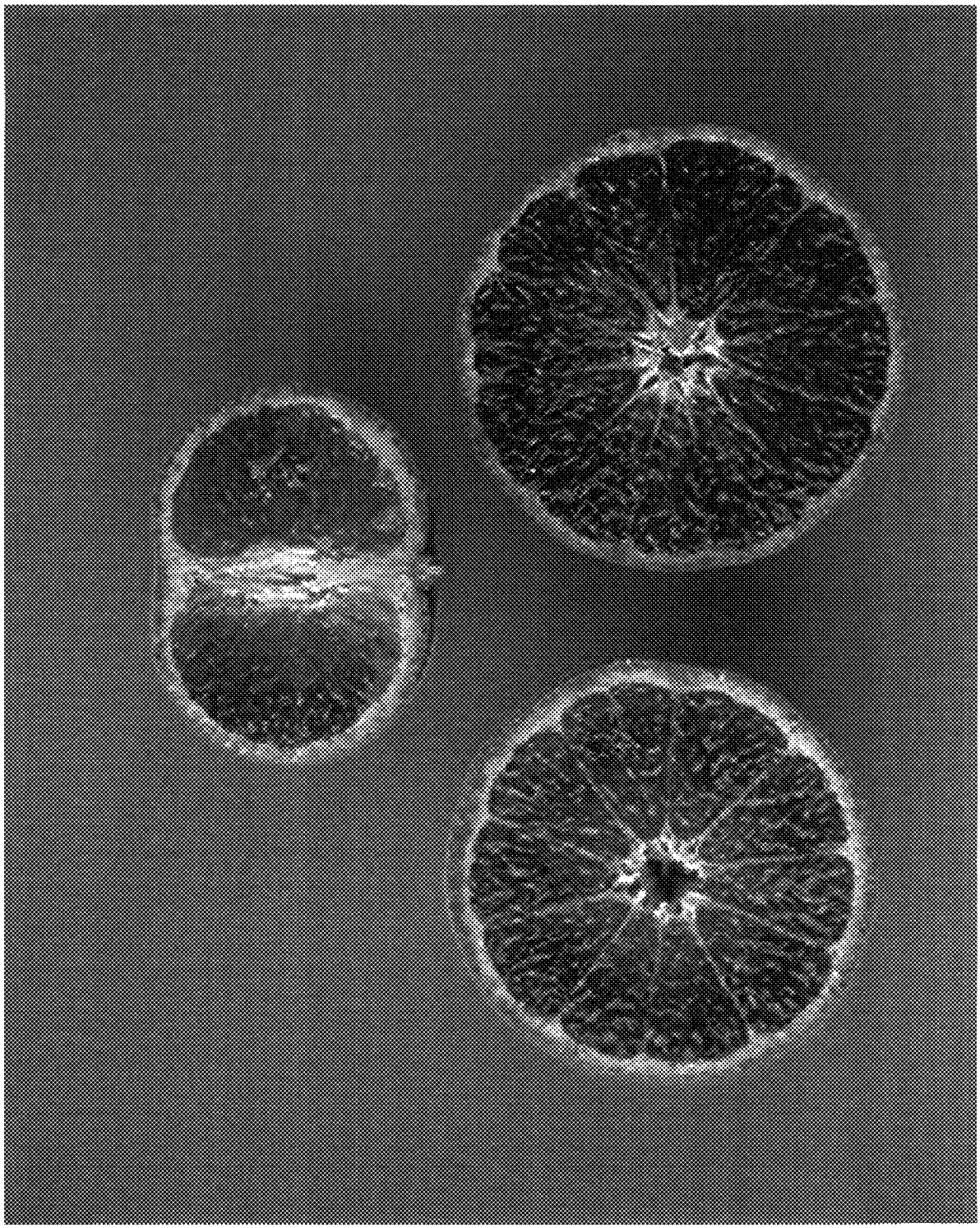
FIG. 2 is a color photograph showing an overall perspective view of several specimens of typical fruit without seeds cut transversely and longitudinally.
Figure 3:
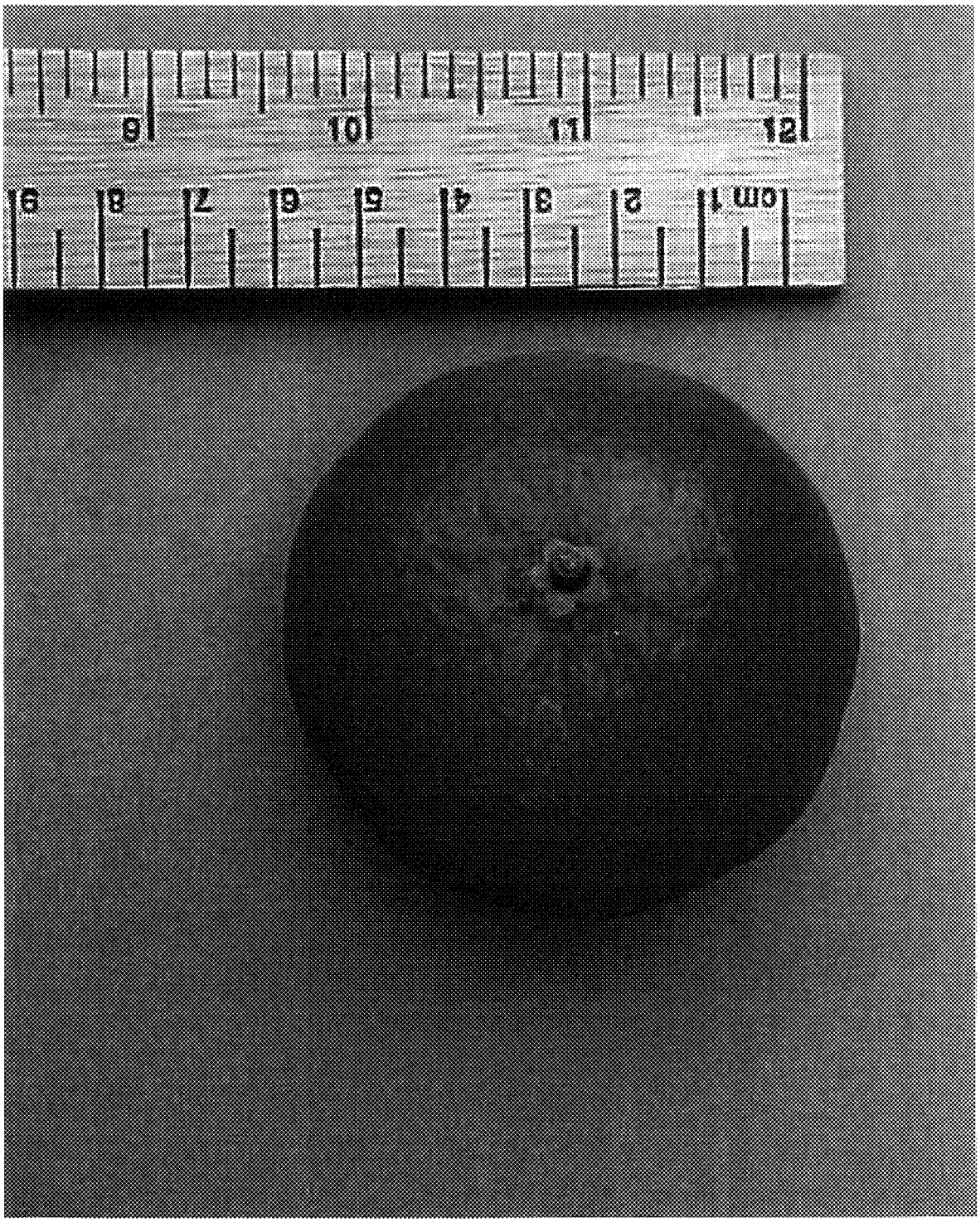
FIG. 3 is a color photograph showing a top view (stem end) of a typical fruit of the present invention (with ruler for scale), showing a characteristic calyical 'button'.

*Form.*—Round and flattened (Typical mandarin shape, See FIG. 1). Fruit surface — smooth. Basal (stem end) slightly depressed.

*Base.*—Diameter 20–25 mm (0.8–1 in.).

*Stem.*—Length 10–25 mm (0.4–1 in.).

*Calyx.*—Diameter 10–15 mm (0.4–0.6 in.).

*Apex.*—Slightly raised, Slightly nippled.

*Areole.*—Absent.

*Stylar scar.*—None.

*Rind.*—Surface — smooth. thickess — average 4–8 mm (0.16–0.32 in.) Color: mandarin (2-F-12) at first harvest (January).

The above description of this new variety of mandarins is based on the growing conditions prevalent in the Sicily, Italy and in Riverside, Calif.; variations of the usual magnitude, such as differences in maturity date and production, may be due to cultural practices including irrigation, fertilization, pruning, fruit thinning and primary climate changes as well as soil conditions.

Use — fresh market/juice.

Keeping quality — Similar to late mandarins.

First harvest date: Around January 15$^{th}$ in Sicily, Italy. around early February in Riverside, Southern Calif.

Post harvest disorders are similar to existing mandarin varieties.

Table 1 below compares the fruit skin color, seeds and pollen fertility between fruit harvested from the 'Top Mandarin Seedless' as compared to 'Hernandina' mandarin on Feb. 7th, 2002.

TABLE 1

| Tree | Fruit skin color (Feb. 7, 2002) | Seeds/fruit* (Feb. 7, 2002) | Pollen fertility** |
|---|---|---|---|
| Hernandina Mandarin | mandarin (2-F-12) | 3-12 | 90% |
| Top Mandarin Seedless | mandarin (2-F-12) | 0 | <0.01% |

*500 fruit assessed per tree, 5 trees

**Estimated by acetocarmine staining during flowering in April

Table 2 details some preliminary yield data for grafted trees. Table 3 indicates the typical harvest pattern from the Top Mandarin.

TABLE 2

| | Typical Yield | |
|---|---|---|
| Year | Yield | Average Fruit Size |
| Yr 1 | 0 | |
| Yr 2 | 5 kg | 185 g |
| Yr 3 | 25 kg | 166 g |
| Yr 4 | 80 kg | 158 g |

TABLE 3

| Typical Picking Pattern of the 'Top Mandarin Seedless' mandarin in Sicily, Italy. | | |
|---|---|---|
| First Pick: | 40% of total | End January |
| Second Pick | 40% of total | Mid February* |

(20% of the fruit will be below the first grade quality criteria.)

What is claimed is:

1. A new and distinct variety of a seedless mandarin tree as described and illustrated called 'Top Mandarin Seedless,' that is characterized as a triploid having late fruit production from about the end of January through to about February in the citrus areas of Sicily, Italy and Riverside, Calif., the trees coming into bearing by year 3, the seedless fruit having typically mandarin, flattened round shape with smooth skin texture, and having acceptable rind thickness, a reddish pigmentation in the flesh, acceptable acid-sugar ratios, and an average juice content at harvest of about 40–50%.

* * * * *